(12) United States Patent
Nemoto et al.

(10) Patent No.: US 7,674,614 B2
(45) Date of Patent: Mar. 9, 2010

(54) METHOD OF OPTICALLY RESOLVING RACEMIC ALCOHOLS WITH A BICYCLOOXAOCTANE OR A BICYCOOXAOCTENE RESOLVING REAGENTS

(75) Inventors: Hisao Nemoto, Tokushima (JP); Masayuki Shibuya, Tokushima (JP)

(73) Assignee: Zeon Corporation, Tokyo (JP)

( * ) Notice: Subject to any disclaimer, the term of this patent is extended or adjusted under 35 U.S.C. 154(b) by 504 days.

(21) Appl. No.: 11/683,322

(22) Filed: Mar. 7, 2007

(65) Prior Publication Data

US 2007/0155994 A1   Jul. 5, 2007

Related U.S. Application Data

(62) Division of application No. 10/468,887, filed as application No. PCT/JP02/01644 on Feb. 25, 2002, now abandoned.

(30) Foreign Application Priority Data

Feb. 26, 2001   (JP) ................. 2001-50958

(51) Int. Cl.
*C12P 41/00*   (2006.01)
(52) U.S. Cl. ...................... 435/280; 549/465
(58) Field of Classification Search ............ None
See application file for complete search history.

(56) References Cited

U.S. PATENT DOCUMENTS 3,609,170 A * 9/1971 Cantrall et al. ............ 552/516
3,931,291 A * 1/1976 Horiuchi .................... 560/84
4,996,158 A * 2/1991 Oda et al. .................. 435/280

OTHER PUBLICATIONS

Nemoto. H , A New Alkenyl Ether Giving Acetal with Stereospecific Manner , Tetrahedron Lett., vol. 35, No. 42 (1994), pp. 7785-7788.
Takenori Kusumi et al., Tetrahedron Letters, vol. 35, No. 25, pp. 4397-4400, 1994.
Tadakatsu Mandai el al., Synlett, 2000, No. 6, pp. 862-864.
W. Victor Tuomi et al., J. Org. Chem., 1999, vol. 64. pp. 2638-2647.
Daniewski et al , "A new route to a chiral synthon for the total synthesis of estrone", Synthesis. 1987, vol. 8, pp. 705-708.

* cited by examiner

*Primary Examiner*—Yelena G Gakh
(74) *Attorney, Agent, or Firm*—Birch, Stewart, Kolasch & Birch, LLP

(57) ABSTRACT

An optical resolving reagent comprising at least one of compounds represented by the following formulae (1) and (2) (1) (2) (wherein $R^1$ to $R^8$ each represents hydrogen or $C_{1-20}$ alkyl; $R^9$ represents optionally substituted $C_{1-20}$ alkyl, optionally substituted $C_{1-20}$ alkenyl, formyl, or acyl; and $R^{10}$ represents $C_{1-6}$ alkyl; provided that the molecule represented by the formula (1) is of the cis configuration with respect to $R^9$ and $OR^{10}$); and a method of optically resolving with the optical resolving reagent an alcohol having an asymmetric carbon atom in the molecule and represented by the formula (3): $(R^{11})(R^{12})(R^{13})COH$ (wherein $R^{11}$, $R^{12}$, and $R^{13}$ each represents hydrogen or optionally substituted $C_{1-20}$ alkyl, provided that at least one of $R^{11}$, $R^{12}$, and $R^{13}$ is not hydrogen). The method of optical resolution is highly suitable for general purposes. By the method, a mixture of optical isomers of any of various alcohols can be optically resolved easily and industrially advantageously.

(1)

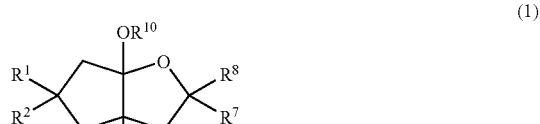

(2)

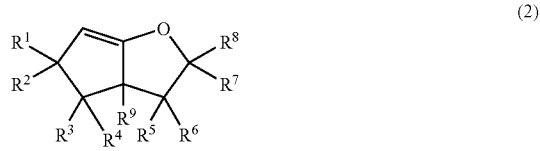

10 Claims, No Drawings

METHOD OF OPTICALLY RESOLVING RACEMIC ALCOHOLS WITH A BICYCLOOXAOCTANE OR A BICYCOOXAOCTENE RESOLVING REAGENTS

This application is a Divisional of application Ser. No. 10/468,887 filed on Aug. 26, 2003 now abandoned and for which priority is claimed under 35 U.S.C. §120. Application Ser. No. 10/468,887 is the national phase of PCT International Application No. PCT/JP02/01644 filed on Feb. 25, 2002 under 35 U.S.C. §371. The entire contents of each of the above-identified applications are hereby incorporated by reference.

TECHNICAL FIELD

The present invention relates to an optical resolving reagent comprising a bicyclo[3.3.0]-1-oxaoctane compound or a bicyclo[3.3.0]-1-oxa-6-octene compound and to a method for optically resolving an alcohol with the optical resolving reagent.

BACKGROUND ART

Many physiologically active substances such as pharmaceuticals, agricultural chemicals, perfumes, and sweeteners comprise a partial structure of alcohol having an asymmetric carbon atom. Optical isomers can be present in such a compound. However, there may be a significant difference in the degree of physiological activity among these optical isomers. Some isomers exhibit physiological activity quite different from others. Therefore, development of a method for separating an optical isomer mixture of an alcohol or a compound having a partial structure of alcohol (hereinafter both simply referred to as "alcohol") easily and surely has been desired.

However, the mixture can rarely be separated into two optical isomers without being influenced by an external optically active factor. Spontaneous resolution or the like rarely occurs. There are no general rules for separating the mixture. Accordingly, in almost all cases, it is highly difficult to assess whether or not an optical isomer mixture of an alcohol can be separated into optically active compounds. The mixture is not easily separated in almost all cases.

As an example of optically resolving an alcohol, Synlett., (6), 862 (2000), J. Org. Chem., 64, 2638 (1999), and the like describe a method comprising allowing one of optical isomers to remain as the alcohol and transforming the other optical isomer into an ester derivative in a natural optically active environment (for example, internal organs of animals containing an esterified enzyme or hydrolyzed enzyme). However, since such an enzyme does not have chemical stability, in particular, thermal stability, the enzyme cannot be used under high temperature conditions. Further, it is difficult for the enzyme to be generally and widely accepted due to its high cost and difficulty in procuring in a large amount.

Tetrahedron Lett., 35, 4397 (1994) reported an experiment in which an ester prepared by condensing a carboxylic acid having an asymmetric carbon atom with an alcohol was separated into individual diastereomers by silica gel column chromatography. In principle, this is optical resolution of an alcohol. However, since there are no general rules or principles for producing a highly separable diastereomer mixture, the method cannot be generally applied.

The present invention has been achieved in view of such a situation. Accordingly, the present invention provides a novel optical resolving reagent that can optically resolve an optical isomer mixture of an alcohol, having an asymmetric carbon atom in the molecule, easily and industrially advantageously, and a method for optically resolving an alcohol using the optical resolving reagent.

DISCLOSURE OF THE INVENTION

The present inventors have already reported that an alcohol-addition acetal compound can be obtained at a high yield by reacting an oxaoctane compound having an acetal structure or alkenyl ether structure in the molecule with an alcohol (Tetrahedron Lett., 35, 7785 (1994)). The present inventors have applied this reaction to an alcohol having an asymmetric carbon atom in the molecule (optical isomer mixture) to obtain an alcohol-addition acetal compound at a high yield. The present inventors have found that an acetal compound obtained as a diastereomer mixture can be separated into individual diastereomers using a convenient separation means and that an optically active alcohol can be isolated from the resulting diastereomers at a high yield. These findings have led to the completion of the present invention.

Accordingly, a first object of the present invention is to provide an optical resolving reagent comprising at least one of the compounds of the following formula (1) or (2):

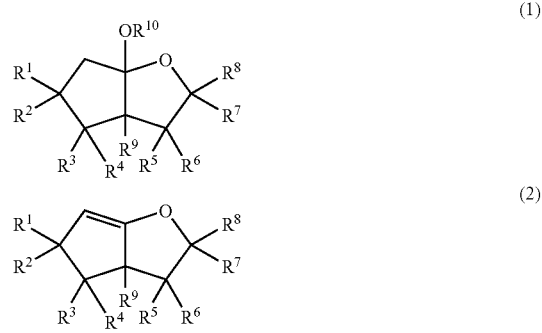

wherein $R^1$-$R^8$ individually represent a hydrogen atom or an alkyl group having 1-20 carbon atoms, $R^9$ represents a substituted or unsubstituted alkyl group having 1-20 carbon atoms, substituted or unsubstituted alkenyl group having 1-20 carbon atoms, formyl group, or an acyl group, and $R^{10}$ represents an alkyl group having 1-6 carbon atoms, provided that a $R^9$ group and a $OR^{10}$ group are cis-configured.

The optical resolving reagent of the present invention preferably comprises any one of the compounds in which $R^1$-$R^8$ are individually a hydrogen atom or methyl group, with the compounds having a hydrogen atom for all $R^1$-$R^8$ groups being more preferable.

The optical resolving reagent of the present invention preferably comprises any one of the compounds in which $R^9$ is an allyl group or a group that can be derived from an allyl group, and more preferably either an allyl group or diphenylmethyl group.

A second object of the present invention is to provide a method for optically resolving an alcohol of the formula (3):

$$(R^{11})(R^{12})(R^{13})COH \qquad (3)$$

wherein $R^{11}$, $R^{12}$, and $R^{13}$ individually represent a hydrogen atom or a substituted or unsubstituted alkyl group having 1-20 carbon atoms, provided that at least one of $R^{11}$, $R^{12}$, and $R^{13}$ is not a hydrogen atom, the method comprising:

a step of reacting one compound of the above formula (1) or (2) with an optical isomer mixture of an alcohol having an asymmetric carbon atom in the molecule of the formula (3) to obtain a diastereomer mixture of the formula (4):

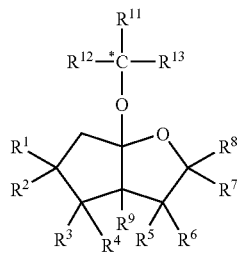 (4)

wherein $R^1$-$R^{13}$ are the same as defined above, * represents an asymmetric carbon atom, and a $R^9$ group and a $OC(R^{11})(R^{12})(R^{13})$ group are cis-configured, a step of separating the resulting diastereomer mixture of the formula (4) into individual diastereomers, and a step of reacting the separated diastereomers with an alcohol of the formula, $R^{14}OH$, wherein $R^{14}$ represents an alkyl group having 1-6 carbon atoms, to obtain an optically active alcohol of the above formula (3).

In the method for optical resolution of the present invention, a compound in which $R^1$-$R^8$ are individually a hydrogen atom or methyl group is preferably used. A compound in which all $R^1$-$R^8$ groups are a hydrogen atom is more preferably used.

In the method for optical resolution of the present invention, a compound in which $R^9$ is an allyl group or a group that can be derived from an allyl group is preferably used. A compound in which $R^9$ is an allyl group or diphenylmethyl group is more preferably used.

The method for optical resolution of the present invention preferably comprises optically resolving an optical isomer mixture of an alcohol having an asymmetric carbon atom in the molecule of the formula (3-1):

 (3-1)

wherein $R^{11a}$ and $R^{12a}$ respectively represent the same groups as defined for $R^{11}$ and $R^{12}$ excluding a hydrogen atom, or an optical isomer mixture of a primary alcohol having an asymmetric carbon atom in the molecule of the formula (3-2):

 (3-2)

wherein $R^{11b}$ represents a substituted or unsubstituted alkyl group having 1-20 carbon atoms and having an asymmetric carbon atom.

In the method for optical resolution of the present invention, an acid catalyst is preferably present in the reaction system in the step of reacting any one of the compounds of the above formula (1) or (2) with the alcohol of the formula (3) to obtain the compound of the formula (4).

In the method for optical resolution of the present invention, an alcohol of the formula, $R^{14}OH$, wherein $R^{14}$ is the same as $R^{10}$, is more preferably used.

The method for optical resolution of the present invention preferably comprises collecting the compound of the above formula (1) or (2) to reuse the compound as an optical resolving reagent after the step of obtaining the optically active alcohol of the above formula (3).

BEST MODE FOR CARRYING OUT THE INVENTION

The optical resolving reagent of the present invention comprises at least one of the compounds of the above formula (1) or (2).

The compound of the above formula (1) or (2) has a (pentacyclic+pentacyclic) skeleton. It is known that a $R^9$ group and an $OR^{10}$ group are cis-configured in a compound having such a skeleton (Tetrahedron Lett., 35, 7785 (1994)). Therefore, if $R^1$, $R^3$, $R^5$, and $R^7$ are respectively the same as $R^2$, $R^4$, $R^6$, and $R^8$, the compound of the above formula (1) and the compound of the above formula (2) can respectively have two optical isomers [(1-1 and 1-2), (2-1 and 2-2)].

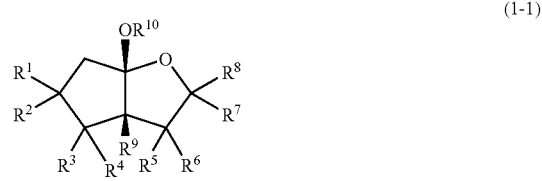 (1-1)

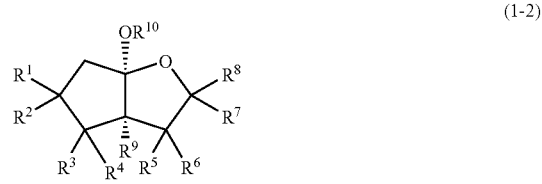 (1-2)

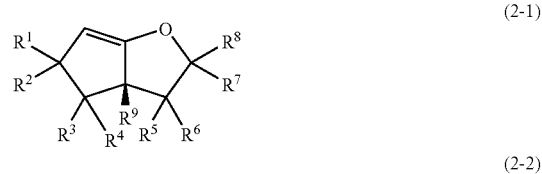 (2-1)

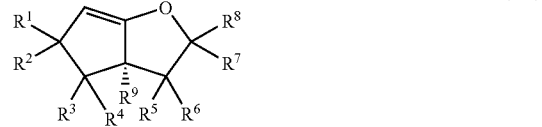 (2-2)

In the present invention, any one of these optical isomers may be used. Alternatively, an optical isomer mixture of the compound of the formula (1-1) and the compound of the formula (1-2) or an optical isomer mixture of the compound of the formula (2-1) and the compound of the formula (2-2) may be used as an optical resolving reagent without separating the mixture into individual optical isomers.

In the above formulas, $R^1$-$R^8$ individually represent a hydrogen atom or a substituted or unsubstituted alkyl group having 1-20 carbon atoms Examples of the substituted or unsubstituted alkyl group having 1-20 carbon atoms include a methyl group, ethyl group, n-propyl group, isopropyl group, n-butyl group, sec-butyl group, isobutyl group, n-pentyl group, n-hexyl group, n-octyl group, n-nonyl group, and n-decyl group. Examples of the substituent for these groups include a hydroxyl group; alkoxy groups such as a methoxy group and ethoxy group; alkylthio groups such as a methylthio group and ethylthio group; halogen atoms such as a fluorine atom and chlorine atom; and substituted or unsubstituted phenyl groups such as a phenyl group, 2-chlorophenyl group, 3-methoxyphenyl group, and 4-methylphenyl group. $R^1$-$R^8$ may respectively have a plurality of the same or different substituents.

Of these, a compound in which $R^1$-$R^8$ are individually a hydrogen atom or methyl group is preferable, since the compound can be easily made available or produced. A compound in which all $R^1$-$R^8$ groups are a hydrogen atom is more preferable.

$R^9$ represents a substituted or unsubstituted alkyl group having 1-20 carbon atoms, substituted or unsubstituted alkenyl group, formyl group, or acyl group.

As examples of the substituted or unsubstituted alkyl group having 1-20 carbon atoms, the above substituted or unsubstituted alkyl groups having 1-20 carbon atoms of $R^1$-$R^8$ can be given.

Examples of the substituted or unsubstituted alkenyl group include an allyl group, isopropenyl group, 1-propenyl group, 1-butenyl group, and 2-butenyl group. Examples of the substituent for these groups include a hydroxyl group; alkoxy groups such as a methoxy group and ethoxy group; alkylthio groups such as a methylthio group and ethylthio group; halogen atoms such as a fluorine atom and chlorine atom; and substituted or unsubstituted phenyl groups such as a phenyl group, 2-chlorophenyl group, 3-methoxyphenyl group, and 4-methylphenyl group.

Examples of the acyl group include an acetyl group, propionyl group, benzoyl group, 2-chlorobenzoyl group, 4-methylbenzoyl group, and 2,4-dimethoxybenzoyl group, $R^9$ may have a plurality of the same or different substituents.

Of these, $R^9$ is preferably an allyl group or an alkyl group having 1-3 carbon atoms which may have a substituent that can be derived from an allyl group. The "substituent that can be derived from an allyl group" refers to a group which can be derived and synthesized from an allyl group using various chemical reactions. There are no specific limitations to the chemical reaction used inasmuch as the reaction conditions ensure the chemical stability of a bicyclooxaoctane ring. Specific examples of the chemical reaction include a dislocation reaction, reduction reaction, oxidation reaction, and Grignard reaction.

In the dislocation reaction, palladium complexes such as dichlorobis(benzonitrile)palladium can be used as a dislocation catalyst, for example. In the reduction reaction, reducing agents such as a metal lithium-ammonium reducing agent, lithium aluminum hydride, diisobutylaluminum hydride, and sodium borohydride can be used. A catalytic hydrogenation reduction using hydrogenation catalysts such as palladium-carbon may be employed. In the oxidation reaction, oxidizing agents such as ozone, manganese dioxide, potassium permanganate, chromic acid, and dichromate can be used. In the Grignard reaction, various Grignard reaction agents such as methylmagnesium bromide, ethylmagnesium bromide, and phenylmagnesium bromide can be used.

Examples of the allyl group or the substituent that can be derived from the allyl group include a propyl group; 1-propenyl group; formyl group; 1-hydroxyalkyl groups such as a hydroxymethyl group, 1-hydroxyethyl group, 1-hydroxyisopropyl group, and 1-hydroxydiphenylmethyl group; α-hydroxyaralkyl groups such as an α-hydroxybenzyl group; acyl groups such as an acetyl group, propionyl group, and benzoyl group; and aralkyl groups such as a benzyl group and diphenylmethyl group.

Of these, $R^9$ is more preferably an allyl group or diphenylmethyl group, since a target product can be obtained at a high yield and can exhibit excellent properties as an optical resolving reagent of an alcohol.

The optical isomer mixture of the compound of the formula (1) can be produced according to the method described in Tetrahedron Lett., 35, 7785 (1994), for example. A common production route of the mixture is shown as follows.

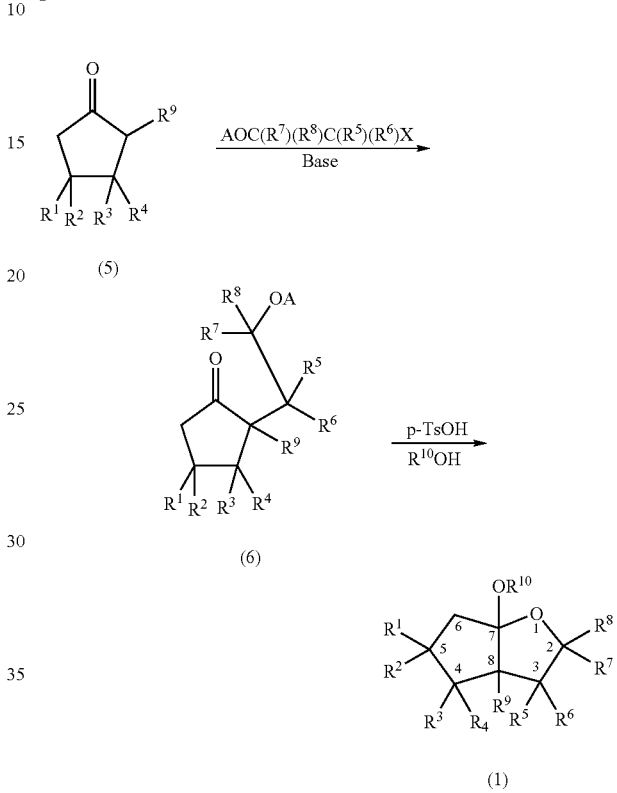

wherein X represents a halogen atom, A represents a protective group for the hydroxyl group such as an acetyl group, and $R^1$-$R^9$ are the same as defined above.

Specifically, the compound of the formula (1) can be obtained by reacting a cyclopentanone derivative of the formula (5) with a halide of the formula, $AOC(R^7)(R^8)C(R^5)(R^6)X$, in the presence of a base to obtain an intermediate of the formula (6) and reacting the intermediate with an alcohol of the formula, $R^{10}OH$, in the presence of an acid catalyst such as p-toluenesulfonic acid (p-TsOH).

$R^{10}$ herein represents a substituted or unsubstituted alkyl group having 1-6 carbon atoms. Examples of the substituted or unsubstituted alkyl group having 1-6 carbon atoms include a methyl group, ethyl group, n-propyl group, isopropyl group, n-butyl group, sec-butyl group, t-butyl group, n-pentyl group, and n-hexyl group. Examples of the substituent for these groups include alkoxy groups such as a methoxy group and ethoxy group; alkylthio groups such as a methylthio group and ethylthio group; halogen atoms such as a fluorine atom and chlorine atom; and substituted or unsubstituted phenyl groups such as a phenyl group, 2-chlorophenyl group, 3-methoxyphenyl group, and 4-methylphenyl group. $R^{10}$ may have a plurality of the same or different substituents.

Specific examples of the compound of the formula (1) include 7-methoxy-8-methyl-bicyclo[3.3.0]-1-oxaoctane, 7-ethoxy-8-methyl-bicyclo[3.3.0]-1-oxaoctane, 7-n-propoxy-8-methyl-bicyclo[3.3.0]-1-oxaoctane, 7-isopropoxy-8-methyl-bicyclo[3.3.0]-1-oxaoctane, 7-t-butoxy-8-methyl-bicyclo[3.3.0]-1-oxaoctane, 7-methoxy-8-ethyl-bicyclo[3.3.0]-1-oxaoctane, 7-ethoxy-8-ethyl-bicyclo[3.3.0]-1-oxaoctane, 7-n-propoxy-8-ethyl-bicyclo[3.3.0]-1-oxaoctane, 7-isopropoxy-8-ethyl-bicyclo[3.3.0]-1-oxaoctane, 7-t-butoxy-8-ethyl-bicyclo[3.3.0]-1-oxaoctane, 7-methoxy-8-n-propyl-bicyclo[3.3.0]-1-oxaoctane, 7-ethoxy-8-n-propyl-bicyclo[3.3.0]-1-oxaoctane, 7-n-propoxy-8-n-propyl-bicyclo[3.3.0]-1-oxaoctane, 7-isopropoxy-8-n-propyl-bicyclo[3.3.0]-1-oxaoctane, 7-t-butoxy-5-n-propyl-bicyclo[3.3.0]-1-oxaoctane, 7-methoxy-8-isopropyl-bicyclo[3.3.0]-1-oxaoctane, 7-ethoxy-8-isopropyl-bicyclo[3.3.0]-1-oxaoctane, 7-n-propoxy-8-isopropyl-bicyclo[3.3.0]-1-oxaoctane, 7-isopropoxy-8-isopropyl-bicyclo[3.3.0]-1-oxaoctane, 7-t-butoxy-8-isopropyl-bicyclo[3.3.0]-1-oxaoctane, 7-methoxy-8-methoxymethyl-bicyclo[3.3.0]-1-oxaoctane, 7-ethoxy-8-methoxymethyl-bicyclo[3.3.0]-1-oxaoctane, 7-n-propoxy-8-methoxymethyl-bicyclo[3.3.0]-1-oxaoctane, 7-isopropoxy-8-methoxymethyl-bicyclo[3.3.0]-1-oxaoctane, 7-t-butoxy-8-methoxymethyl-bicyclo[3.3.0]-1-oxaoctane, 7-methoxy-8-methylthiomethyl-bicyclo[3.3.0]-1-oxaoctane, 7-methoxy-8-ethylthiomethyl-bicyclo[3.3.0]-1-oxaoctane, 7-n-propoxy-8-ethoxymethyl-bicyclo[3.3.0]-1-oxaoctane, 7-isopropoxy-8-propylthiomethyl-bicyclo[3.3.0]-1-oxaoctane, 7-t-butoxy-8-ethoxymethyl-bicyclo[3.3.0]-1-oxaoctane, 7-methoxy-8-allyl-bicyclo[3.3.0]-1-oxaoctane, 7-ethoxy-8-allyl-bicyclo[3.3.0]-1-oxaoctane, 7-n-propoxy-8-allyl-bicyclo[3.3.0]-1-oxaoctane, 7-isopropoxy-8-allyl-bicyclo[3.3.0]-1-oxaoctane, 7-t-butoxy-8-allyl-bicyclo[3.3.0]-1-oxaoctane, 7-methoxy-8-allyl-bicyclo[3.3.0]-1-oxaoctane, 7-ethoxy-8-allyl-bicyclo[3.3.0]-1-oxaoctane, 7-n-propoxy-8-allyl-bicyclo[3.3.0]-1-oxaoctane, 7-isopropoxy-8-allyl-bicyclo[3.3.0]-1-oxaoctane, 7-t-butoxy-8-allyl-bicyclo[3.3.0]-1-oxaoctane, 7-methoxy-8-benzyl-bicyclo[3.3.0]-1-oxaoctane, 7-ethoxy-8-benzyl-bicyclo[3.3.0]-1-oxaoctane, 7-n-propoxy-8-benzyl-bicyclo[3.3.0]-1-oxaoctane, 7-isopropoxy-8-benzyl-bicyclo[3.3.0]-1-oxaoctane, 7-t-butoxy-8-benzyl-bicyclo[3.3.0]-1-oxaoctane, 7-methoxy-8-benzyl-bicyclo[3.3.0]-1-oxaoctane, 7-ethoxy-8-benzyl-bicyclo[3.3.0]-1-oxaoctane, 7-n-propoxy-8-benzyl-bicyclo[3.3.0]-1-oxaoctane, 7-isopropoxy-8-benzyl-bicyclo[3.3.0]-1-oxaoctane, 7-t-butoxy-8-benzyl-bicyclo[3.3.0]-1-oxaoctane, 7-methoxy-8-diphenylmethyl-bicyclo[3.3.0]-1-oxaoctane, 7-ethoxy-8-diphenylmethyl-bicyclo[3.3.0]-1-oxaoctane, 7-n-propoxy-8-diphenylmethyl-bicyclo[3.3.0]-1-oxaoctane, 7-isopropoxy-8-diphenylmethyl-bicyclo[3.3.0]-1-oxaoctane, 7-t-butoxy-8-diphenylmethyl-bicyclo[3.3.0]-1-oxaoctane, 7-methoxy-8-(1-propenyl)-bicyclo[3.3.0]-1-oxaoctane, 7-ethoxy-8-(1-propenyl)-bicyclo[3.3.0]-1-oxaoctane, 7-n-propoxy-8-(1-propenyl)-bicyclo[3.3.0]-1-oxaoctane, 7-isopropoxy-8-(1-propenyl)-bicyclo[3.3.0]-1-oxaoctane, 7-t-butoxy-8-(1-propenyl)-bicyclo[3.3.0]-1-oxaoctane, 7-methoxy-8-formyl-bicyclo[3.3.0]-1-oxaoctane, 7-methoxy-8-benzoyl-bicyclo[3.3.0]-1-oxaoctane, 7-methoxy-8-phenylhydroxymethyl-bicyclo[3.3.0]-1-oxaoctane, 7-methoxy-8-diphenylhydroxymethyl-bicyclo[3.3.0]-1-oxaoctane, 7-methoxy-8-acetyl-bicyclo[3.3.0]-1-oxaoctane, 7-methoxy-2-methyl-8-allyl-bicyclo[3.3.0]-1-oxaoctane, 7-ethoxy-2-methyl-8-allyl-bicyclo[3.3.0]-1-oxaoctane, 7-n-propoxy-2-methyl-8-allyl-bicyclo[3.3.0]-1-oxaoctane, 7-isopropoxy-2-methyl-8-allyl-bicyclo[3.3.0]-1-oxaoctane, and 7-t-butoxy-2-methyl-8-allyl-bicyclo[3.3.0]-1-oxaoctane.

The compound of the above formula (2) can be derived from the compound of the formula (1) according to the following reaction equation (see Tetrahedron Lett., 35, 7785 (1994)). The reaction is known to proceed while the steric configuration of the compound is maintained.

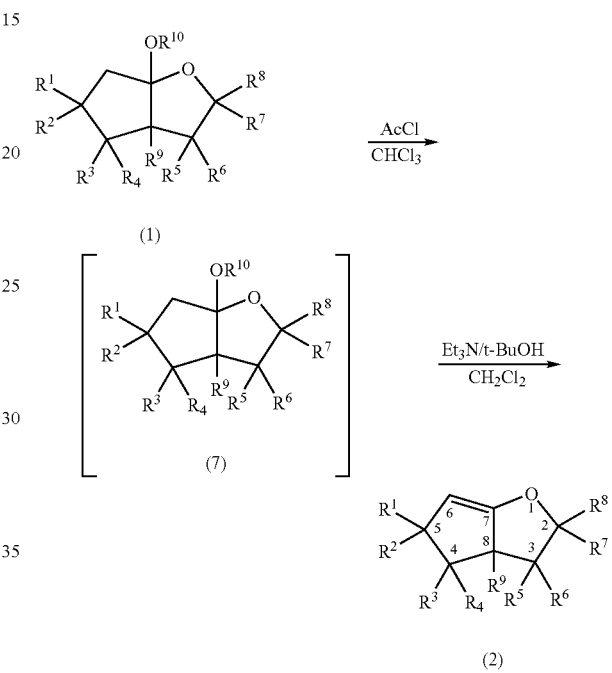

wherein $R^1$-$R^{10}$ are the same as defined above.

Specifically, the compound of the formula (2) can be obtained by reacting the compound of the formula (1) with acetyl chloride in an inert solvent to obtain an intermediate (not isolated) of the formula (7) and reacting the intermediate with t-butyl alcohol (t-BuOH) and triethylamine ($Et_3N$).

Examples of the compound of the formula (2) include 8-methyl-bicyclo[3.3.0]-1-oxa-6-octene, 8-ethyl-bicyclo[3.3.0]-1-oxa-6-octene, 8-n-propyl-bicyclo[3.3.0]-1-oxa-6-octene, 8-allyl-bicyclo[3.3.0]-1-oxa-6-octene, 8-benzyl-bicyclo[3.3.0]-1-oxa-6-octene, 8-diphenylmethyl-bicyclo[3.3.0]-1-oxa-6-octene, 8-(1-propenyl)-bicyclo[3.3.0]-1-oxa-6-octene, 8-methoxymethyl-bicyclo[3.3.0]-1-oxa-6-octene, 8-formyl-bicyclo[3.3.0]-1-oxa-6-octene, 8-benzoyl-bicyclo[3.3.0]-1-oxa-6-octene, 8-acetyl-bicyclo[3.3.0]-1-oxa-6-octene, 8-phenylhydroxymethyl-bicyclo[3.3.0]-1-oxa-6-octene, and 8-diphenylhydroxymethyl-bicyclo[3.3.0]-1-oxa-6-octene.

Next, the method for optically resolving an alcohol of the present invention is described below. An outline of the method for optically resolving an alcohol of the present invention is shown as follows.

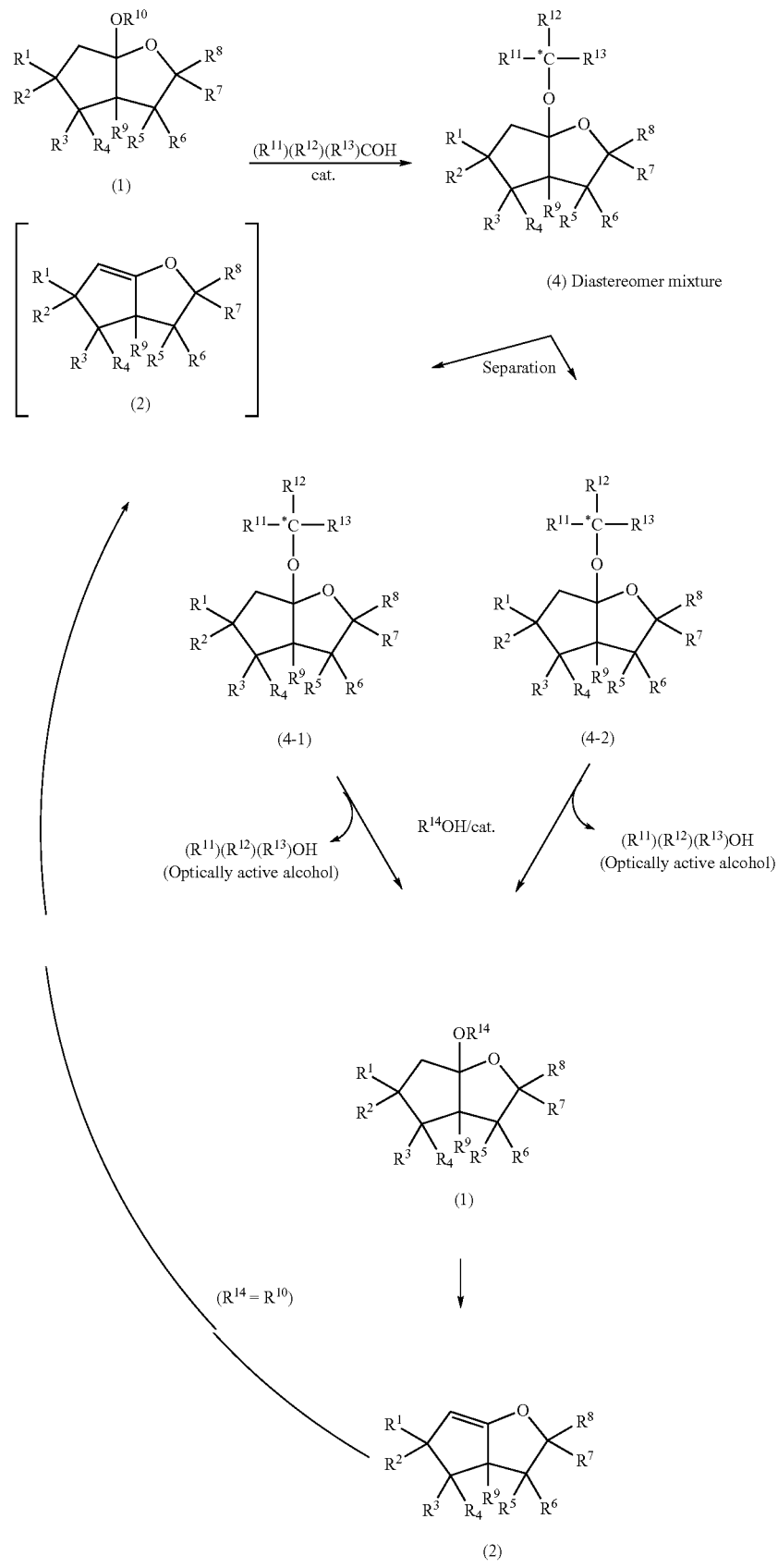

The method for optical resolution of the present invention comprises (i) a step of reacting a compound of the formula (1) or (2) with an optical isomer mixture of an alcohol having an asymmetric carbon atom in the molecule of the formula (3), $(R^{11})(R^{12})(R^{13})COH$, to obtain a diastereomer mixture of the formula (4), (ii) a step of separating the resulting diastereomer mixture of the formula (4) into individual diastereomers, and (iii) a step of reacting the separated diastereomers with an alcohol of the formula, $R^{14}OH$, to obtain an optically active alcohol of the formula (3).

In the formula (3), $R^{11}$, $R^{12}$, and $R^{13}$ individually represent a hydrogen atom or a substituted or unsubstituted alkyl group having 1-20 carbon atoms, provided that at least one of $R^{11}$, $R^{12}$, and $R^{13}$ is not a hydrogen atom.

As examples of the substituted or unsubstituted alkyl group having 1-20 carbon atoms, the specific substituted or unsubstituted alkyl groups having 1-20 carbon atoms given as examples of $R^1$-$R^8$ can be given.

There are no specific limitations to the alcohol of the above formula (3) inasmuch as the alcohol has an asymmetric carbon atom in the molecule., A primary alcohol, secondary alcohol, or tertiary alcohol may be used. In the present invention, a secondary alcohol of the formula (3-1), $(R^{11a})(R^{12a})CHOH$, and a primary alcohol of the formula (3-2), $(R^{11b})CH_2OH$, are preferable. $R^{11a}$ refers to the same groups as defined for $R^{11}$ excluding a hydrogen atom $R^{12a}$ refers to the same groups as defined for $R^{12}$ excluding a hydrogen atom $R^{11b}$ represents a substituted or unsubstituted alkyl group having 1-20 carbon atoms and having an asymmetric carbon atom. Examples of $R^{11b}$ include a 1-methylpropyl group, 1-ethylpropyl group, 1-methylbutyl group, 1-ethylbutyl group, 2-methylbutyl group, 1-methylpentyl group, 2-methylpentyl group, 1-ethylpentyl group, 2-ethylpentyl group, 1-ethylhexyl group, 2-ethylhexyl group, and 2-propylhexyl group.

The step (i) of reacting an optically active compound of the formula (1) or (2) with an optical isomer mixture of an alcohol of the formula (3) is carried out by mixing and stirring both compounds in a suitable solvent.

There are no specific limitations to the solvent used for this reaction inasmuch as the solvent is nonprotonic. Examples of the solvent include aromatic hydrocarbons such as benzene, toluene, xylene, chlorobenzene, benzonitrile, and dichlorobenzene; aliphatic hydrocarbons such as pentane, hexane, heptane, octane, cyclohexane, cycloheptane, and petroleum ether; esters such as ethyl acetate, propyl acetate, and butyl acetate; halogenated hydrocarbons such as dichloromethane, chloroform, carbon tetrachloride, 1,2-dichloroethane, and 1,1,2-trichloroethane; ethers such as diethyl ether, tetrahydrofuran, 1,4-dioxane, and 1,2-dimethoxyethane; and amides such as N,N-dimethylformamide, N,N-dimethylacetamide, and N-methylpyrrolidone. These solvents may be used either individually or in combination of two or more. In the present invention, it is preferable to use organic solvents with a comparatively low boiling point including aromatic hydrocarbons such as benzene, toluene, and xylene; aliphatic hydrocarbons such as pentane, hexane, heptane, octane, cyclohexane, cycloheptane, and petroleum ether; and halogenated hydrocarbons such as chloroform and carbon tetrachloride.

In this reaction, an acid catalyst such as pyridinium p-toluenesulfonate (PPTS), p-toluenesulfonic acid (p-TsOH), or montmorillonite or synthetic zeolite is preferably present in the reaction system. The amount of the acid catalyst added is usually 0.0001-1 mol for one mol of the compound of the above formula (1) or (2). The reaction is smoothly carried out in the temperature range of −20° C. to a boiling point of the solvent used, and more preferably in the temperature range of −10° C. to 50° C. The reaction is usually terminated several minutes to dozens of hours after the beginning of reaction.

In the step (ii), the resulting diastereomer mixture of the formula (4) is separated into individual diastereomers. This diastereomer mixture can be easily separated into the individual diastereomers by column chromatography using silica gel, alumina, neutral alumina, or the like.

There are no specific limitations to an eluate for separating the mixture inasmuch as the eluate is an inert solvent to provide a ΔRf value that can allow the mixture to be fully separated into the optical isomers. Examples of the eluate include n-hexane, n-hexane-benzene, n-hexane-diethyl ether, n-hexane-ethyl acetate, n-hexane-acetone, n-hexane-chloroform, n-hexane-dichloromethane, benzene, benzene-ethyl acetate, benzene-diethyl ether, benzene-chloroform, benzene-dichloromethane, benzene-acetone, acetone, chloroform, and dichloromethane.

In the step (iii), each of the separated optical isomers of the formula (4) is reacted with an alcohol of the formula, $R^{14}OH$, to obtain the optically active alcohols of the formula (3), respectively.

This reaction can be carried out under the same conditions as in the case of reacting the compound of the above formula (4) with the alcohol of the above formula (3).

As the alcohol ($R^{14}OH$), an alcohol having 1-6 carbon atoms is preferable. Specific examples of the alcohol include low-boiling point alcohols such as methanol, ethanol, n-propanol, isopropanol, isobutanol, n-butanol, sec-butanol, and t-butanol. Of these, an alcohol in which $R^{14}$ is the same as $R^{10}$ is more preferably used. This is because the reaction product can be easily separated and refined after terminating the reaction and the compound of the formula (1) can be repeatedly used as an optical resolving reagent.

The optically active alcohol of the formula (3) separated in this reaction can be isolated using a conventional refining method such as distillation or column chromatography.

The above reaction proceeds while maintaining the steric configuration of the compound and avoiding a side reaction. Therefore, the compound of the formula (1) or (2) can be collected at a high yield. The collected compound of the formula (1) or (2) may be optionally refined and reused as an optical resolving reagent.

If the optical resolving reagent of the present invention is used, an optical isomer mixture of a compound having a functional group with an asymmetric carbon atom in the molecule and an activated hydrogen, reactive with vinyl ether by an addition reaction, can also be optically resolved, wherein examples of such a compound include thiols, carboxylic acids, sulfonic acids, amines, terminal acetylenes, and β-dicarbonyl compounds.

The compound of the above formula (1) or (2) can be optically resolved by applying the method for optical resolution of the present invention. An outline of the optical resolution is shown in the following scheme.

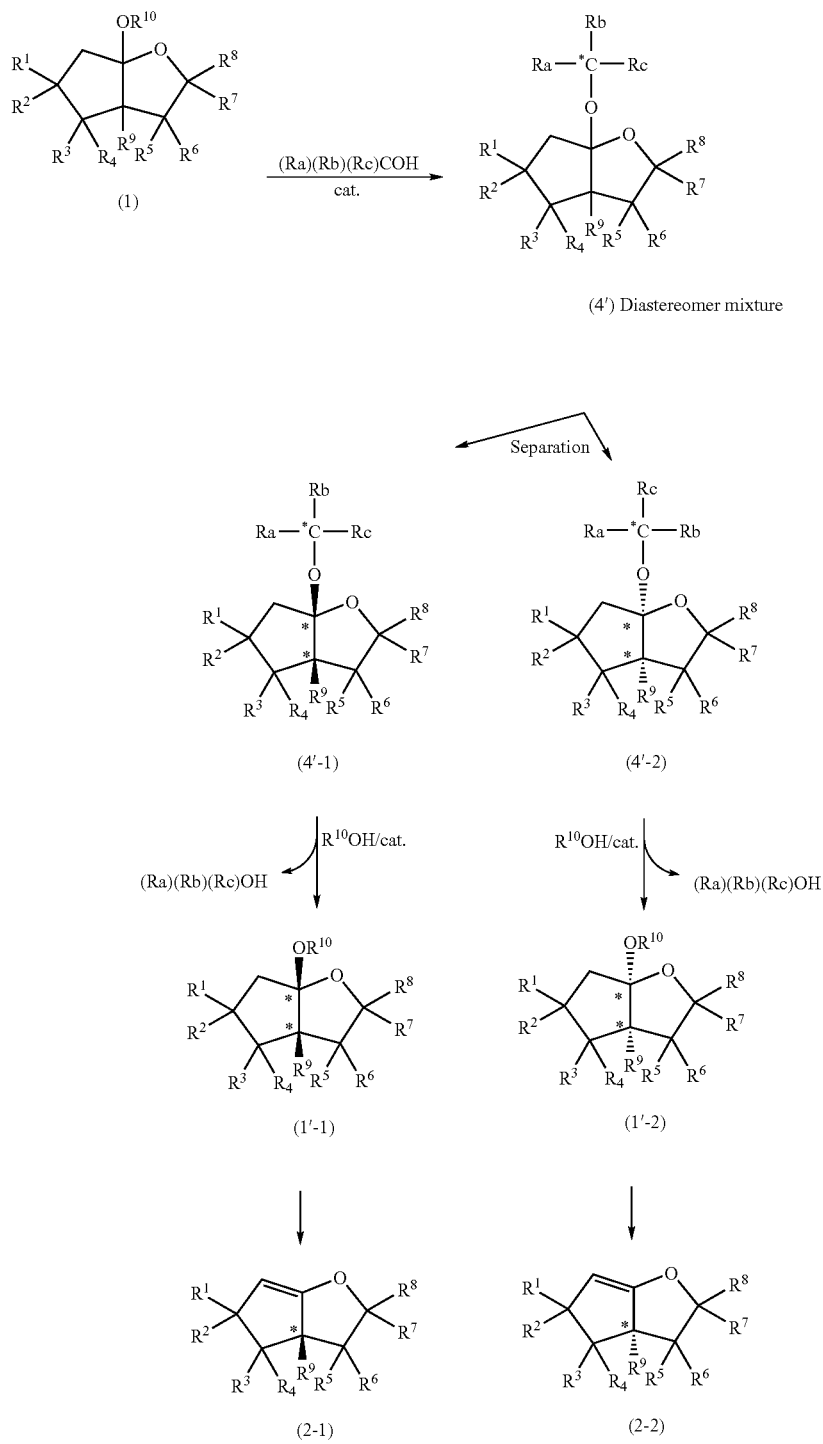

(4') Diastereomer mixture

In the above formulas, $R^1$-$R^{10}$ and * are the same as defined above, and Ra, Rb, and Rc individually represent a hydrogen atom or a substituted or unsubstituted alkyl group. As specific examples of Ra, Rb, and Rc, the compounds respectively the same as those given as examples of $R^{11}$, $R^{12}$, and $R^{13}$ can be given.

The reaction conditions of the method for optically resolving an alcohol of the present invention can be applied to each reaction in the above scheme.

First, an optically active alcohol of the formula (Ra)(Rb)(Rc)COH is reacted with a compound of the formula (1) or (2) to obtain a diastereomer mixture of the formula (4').

Second, the resulting diastereomer mixture of the formula (4') is separated using a conventional separation means such as silica gel column chromatography.

Third, the separated diastereomers (4'-1 and 4'-2) are reacted with an alcohol $R^{14}OH$, wherein $R^{14}$ is the same as defined for $R^{10}$, to obtain optical isomers (1'-1 and 1'-2) of the compound of the formula (1). Optical isomers (2-1 and 2-2) of the compound of the formula (2) can be respectively derived from the resulting optical isomers (1'-1- and 1'-2) using the above-described method.

EXAMPLES

The present invention will be described in more detail by way of examples. The following examples should not be construed as limiting the present invention. Various modifications and variations to the type of a compound of the formula (1) or (2) or an alcohol, reaction solvent, reaction temperature, or the like are possible within the scope of the present invention.

Example 1

Preparation of 7-methoxy-8-(2-propenyl)-bicyclo[3.3.0]-1-oxaoctane (8)

An optical isomer mixture of 7-methoxy-8-(2-propenyl)-bicyclo[3.3.0]-1-oxaoctane (8) as a starting material was synthesized as described in Tetrahedron Lett, 35, 7785 (1994).

Example 2

Preparation of 7-methoxy-8-diphenylmethyl-bicyclo[3.3.0]-1-oxaoctane (14)

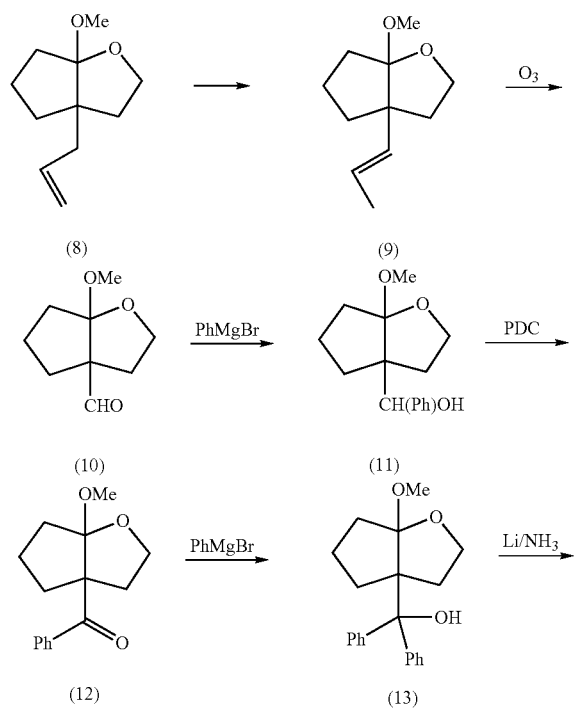

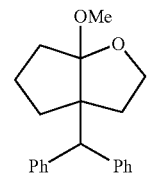

11.8 g (30.8 mmol) of dichlorobis(benzonitrile)palladium (II) is added to a solution of 80.0 g (0.439 mol) of 7-methoxy-8-(2-propenyl)-bicyclo[3.3.0]-1-oxaoctane (8) in 800 ml of benzene at room temperature. The mixture was stirred at the same temperature for 30 minutes. 9 ml of triethylamine was added to the reaction solution and the mixture was stirred for 10 minutes at room temperature. The reaction solution was diluted with diethyl ether and filtered through celite. The filtrate was concentrated under reduced pressure. The resulting residue was purified by silica gel column chromatography (n-hexane:ethyl acetate=20:1) to obtain 64.2 g of 7-methoxy-8-(1-propenyl)-bicyclo[3.3.0]-1-oxaoctane (9) as a colorless oil. The yield was 80%.

The properties data of the resulting compound (9) are shown as follows.

FT-IR (neat): 2,954, 2,882, 2,829, 1,451, 1,316, 1,122, 1,063, 1,013, 970, 911, 836 $cm^{-1}$ $^1$H-NMR ($CDCl_3$, δppm): 5.67 (dd, J=1.3, 15.8 Hz, 1H), 5.47 (dq, J=15.8, 6.3 Hz, 1H), 3.91 (ddd, J=6.0, 7.5, 7.5 Hz, 1H), 3.88 (ddd, J=7.5, 7.5, 7.5 Hz, 1H), 3.29 (s, 3H), 2.12-2.00 (m, 1H), 2.09 (ddd, J=6.0, 7.5, 12.3 Hz, 1H), 1.85-1.62 (m, 5H), 1.84 (ddd, T=7.5, 7.5, 12.3 Hz, 1H), 1.72 (dd, J=1.3, 6.3 Hz, 3H)

EI-MS: m/z 182 ($M^+$).

EI-HRMS: m/z Calcd for $C_{11}H_{18}O_2$: 182.1307. Found: 182.1310.

A stream of ozone-oxygen was circulated in a solution of 55 g (0.302 mol) of the resulting compound (9) in 275 ml of methylene chloride for 16 hours. After ozonization, excessive ozone was discharged from the reaction solution by circulating dry nitrogen in the solution at the same temperature for 30 minutes. 38.3 ml of methyl sulfide was added to the reaction solution and the mixture was stirred until reaching room temperature. The reaction solution was poured into water and the mixture was extracted with methylene chloride. The organic layer was washed with saturated brine, dried over anhydrous potassium carbonate, and filtered. The filtrate was concentrated under reduced pressure. The resulting residue was purified by silica gel column chromatography (n-hexane:ethyl acetate 8:1) to eliminate a bi-product on the high polarity side of the residue. 7-Methoxy-8-formyl-bicyclo[3.3.0]-1-oxaoctane (10) was thus obtained as a colorless oil. This compound was used for the following reaction without purifying.

A THF solution (1 M, 412 ml, 0.412 mol) of phenylmagnesium bromide (PhMgBr) was added dropwise to a solution of the resulting compound (10) in 500 ml of THF at 0° C. The mixture was stirred at the same temperature for 30 minutes. The reaction solution was poured into saturated aqueous solution of ammonium chloride and the mixture was extracted with diethyl ether. The organic layer was washed with saturated brine, dried over anhydrous potassium carbonate, and filtered. The filtrate was concentrated under reduced pressure to obtain 7-methoxy-8-(α-hydroxybenzyl)-bicyclo[3.3.0]-1- oxaoctane (11) as a colorless oil. This compound was used for the following reaction without purifying.

98 g (0.259 mol) of pyridinium dichrochromate (PDC) was added to a solution of the resulting compound (11) in 500 ml of DMF at the room temperature. The mixture was stirred at the same temperature for 48 hours. The reaction solution was poured into water and the mixture was extracted with diethyl ether. The organic layer was washed with saturated brine, dried over anhydrous potassium carbonate, and filtered. The filtrate was concentrated under reduced pressure. The resulting residue was purified by silica gel column chromatography (n-hexane:ethyl acetate=4:1) to obtain 33.5 g of crystals of 7-methoxy-8-benzoyl-bicyclo[3.3.0]-1-oxaoctane (12) as a colorless oil. The yield was 45%.

The properties data of the resulting compound (12) are shown as follows.

FT-IR (KBr): 3,061, 2,978, 2,882, 2,834, 1,670, 1,595, 1,470, 1,438, 1,319, 1,275, 1,216, 1,109, 1,057, 1,028, 949, 885, 823, 772, 710 cm$^{-1}$ $^1$H-NMR (CDCl$_3$, δppm) 7.65-7.60 (m, 2H), 7.45-7.33 (m, 3H), 4.01 (ddd, J=3.4, 8.4, 8.4 Hz, 1H), 3.97 (ddd, J=5.6, 8.4, 8.4 Hz, 1H), 3.32 (s, 3H), 2.79 (ddd, J=3.4, 5.6, 12.4 Hz, 1H), 2.47 (ddd, J=7.3, 10.4, 12.9 Hz, 1H), 2.19 (dddd, J=1.1, 1.1, 6.5, 12.0 Hz, 1H), 2.00 (ddd, J=7.5, 12.0, 12.0 Hz, 1H), 1.95-1.70 (m, 2H), 1.83 (ddd, J=8.4, 8.4, 12.4 Hz, 1H), 1.62 (dddd, J=1.1, 2.5, 6.5, 12.9 Hz, 1H)

Elemental analysis: Calcd for C$_{15}$H$_{18}$O$_3$: C, 73.15; H, 7.37. Found: C, 73.02; H, 7.51(%).

A THF solution (1 M, 40 ml, 40 mmol) of phenylmagnesium bromide was added dropwise to a solution of 4.7 g (19.1 mol) of the resulting compound (12) in 100 ml of THF at 0° C. The mixture was stirred at the same temperature for 30 minutes. The reaction solution was poured into saturated aqueous solution of ammonium chloride and the mixture was extracted with diethyl ether. The organic layer was washed with saturated brine, dried over anhydrous potassium carbonate, and filtered. The filtrate was concentrated under reduced pressure. The resulting residue was purified by silica gel column chromatography (n-hexane:ethyl acetate=4:1) to obtain 5.12 g of 7-methoxy-8-hydroxydiphenylmethyl-bicyclo[3.3.0]-1-oxaoctane (13) as a colorless oil. The yield was 79%.

The properties data of the resulting compound (13) are shown as follows.

FT-IR (KBr): 3,046, 2,995, 2,959, 2,887, 1,446, 1,395, 1,207, 1,113, 1,061, 1,000, 754, 700 cm$^{-1}$ $^1$H-NMR (CDCl$_3$, δppm): 7.46-7.41 (m, 2H), 7.37-7.32 (m, 3H), 7.28-7.14 (m, 6H), 6.19 (s, 1H), 3.97 (ddd, J=4.5, 8.0, 8.0 Hz, 1H), 3.82 (ddd, J=8.0, 8.0, 8.0 Hz, 1H), 3.36 (s, 3H), 2.86 (ddd, J=4.5, 8.0, 12.5 Hz, 1H), 2.69 (ddd, J=9.0, 9.0, 13.5 Hz, 1H), 2.16 (ddd, J=8.0, 8.0, 12.5, 1H), 1.88 (ddd, J=3.5, 13.5, 13.5 Hz, 1H), 1.86 (brdd, J=8.8, 11.4, 1H), 1.21 (dddd, J=1.4, 3.5, 9.0, 9.0, 12.5 Hz, 1H), 0.94 (ddd, J=9.0, 11.4, 11.4 HZ, 1H)

Elemental analysis: Calcd for C$_{21}$H$_{24}$O$_3$: C, 77.75; H, 7.46. Found: C, 77.71; H, 7.70(%).

2 ml of liquid ammonia was added dropwise to a solution of 20 mg (0.0616 mmol) of the resulting compound (13) in 1 ml of THF at −78° C. 10 mg (1.44 mmol) of metal lithium was added to the mixture at the same temperature, followed by stirring for 10 minutes. Ammonium chloride was added to the reaction solution and the reaction was terminated. The mixture was stirred until reaching room temperature. The reaction solution was poured into water and the mixture was extracted with methylene chloride. The organic layer was washed with saturated brine, dried over anhydrous potassium carbonate, and filtered. The filtrate was concentrated under reduced pressure. The resulting residue was purified by silica gel column chromatography (n-hexane:ethyl acetate=8:1) to obtain 15 mg of 7-methoxy-8-diphenylmethyl-bicyclo[3.3.0]-1-oxaoctane (14) as a colorless oil. The yield was 78%.

The properties data of the compound (14) are shown as follows.

FT-IR (KBr): 2,952, 21895, 1,595, 1,497, 1,449, 1,322, 1,122, 1,065, 1,031, 976, 834, 754, 701 cm$^{-1}$ $^1$H-NMR (CDCl$_3$, δppm): 7.40-7.32 (m, 4H), 7.27-7.09 (m, 6H) 4.57 (s, 1H), 3.86 (ddd, J=8.0, 8.0, 8.0 Hz, 1H), 3.82 (ddd, J=5.4, 3.0, 8.0 Hz, 1H), 3.38 (s, 3H), 2.67 (ddd, J=6.4, 9.4, 13.5 Hz, 1H), 2.01 (ddd, J=5.4, 8.0, 12.5 Hz, 1H), 1.96 (ddd, J=8.0, 8.0, 12.5 Hz, 1H), 1.82 (ddd, J=1.9, 8.0, 12.0 Hz, 1H), 1.80 (ddd, J=4.7, 9.4, 13.5 Hz, 1H), 1.49 (ddddd, J=6.4, 8.0, 9.4, 9.4, 12.0 Hz, 1H), 1.03 (ddddd, J=1.9, 4.7, 9.4, 9.4, 12.0 Hz, 1H), 0.90 (ddd, J=9.4, 9.4, 12.0 Hz, 1H)

$^{13}$C-NMR (CDCl$_3$, δppm): 144.5 (C), 142.9 (2×CH), 130.7 (2×CH), 129.6 (2×CH), 128.1 (2×CH), 127.6 (2×CH), 126.0 (CH), 125.8 (CH), 118.0 (C), 65.7 (CH$_2$), 58.0 (C), 54.4 (CH), 50.6 (CH$_3$), 40.1 (CH$_2$), 32.9 (CH$_2$), 31.9 (CH$_2$), 21.0 (CH$_2$)

Elemental analysis: Calcd for C$_{21}$H$_{24}$O$_2$: C, 81.78; H, 7.84. Found: C, 81.62; 7.99(%).

Example 3

Preparation of 8-diphenylmethyl-bicyclo[3.3.0]-1-oxa-6-octene (15)

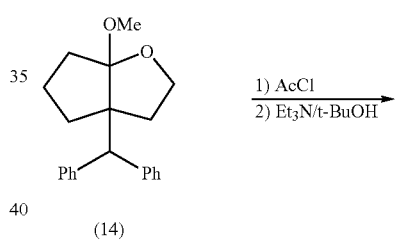

(14)

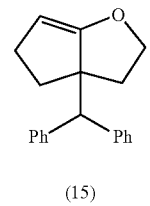

(15)

3.93 g (50 mmol) of acetyl chloride was added dropwise to a solution of 1.54 g (5.0 mmol) of the compound (14) obtained in Example 2 in 8 ml of chloroform at room temperature. The mixture was stirred at the same temperature for 20 hours. Then, chloroform and excess acetyl chloride were evaporated under reduced pressure under anhydrous conditions, then under 0.1 mmHg to complete the evaporation. The residue was diluted with 3 ml of methylene chloride and the solution was immediately used for the following reaction.

The residue solution was added dropwise to a solution of 5.06 g (50.0 mmol) of triethylamine in 13 ml of methylene chloride at room temperature. The mixture was stirred at the same temperature for 30 minutes. The reaction solution was poured into 7.5 ml of a 5 N solution of sodium hydroxide and the mixture was extracted with methylene chloride. Then, the organic layer was dried over anhydrous potassium carbonate and filtered. The filtrate was extracted with methylene chloride. The organic layer was dried over anhydrous potassium carbonate and filtered. The filtrate was concentrated under reduced pressure. The resulting residue was purified by alumina gel column chromatography (n-hexane:diethyl ether=8:1) to obtain 1.14 g of the target compound (15) as white powder crystals. The yield was 82%.

The properties data of the compound (15) are shown as follows.

FT-IR (KBr): 3,078, 3,028, 2,977, 2,940, 2,894, 2,862, 1,674, 1,600, 1,492, 1,450, 1,366, 1,321, 1,206, 1,174, 1,082, 1,028, 987, 928, 750, 702 cm$^{-1}$ $^1$H-NMR (CDCl$_3$, δppm): 7.29 (d, J=4.4 Hz, 4H), 7.26-7.13 (m, 6H), 4.43 (dd, J=1.5, 3.5 Hz, 1H), 4.38 (brdd, J=8.7, 9.0 Hz, 1H), 4.27 (s, 1H), 4.10 (ddd, J=6.2, 8.7, 11.0 Hz, 1H), 2.42 (ddd, J=0.0, 6.2, 12.0 Hz, 1H), 2.25 (brdd, J=6.2, 12.4 Hz, 1H), 2.06 (dddd, J=0.0, 3.5, 9.0, 14.2 Hz, 1H), 1.97 (ddd, J=9.0, 11.0, 12.4 Hz, 1H), 1.91 (ddd, J=9.0, 9.0, 12.0 Hz, 1H), 1.39 (dddd, J=1.5, 9.0, 6.2, 14.2 Hz, 1H)

$^{13}$C-NMR (CDCl$_3$, δppm): 166.3 (C), 142.5 (C), 142.3 (C), 130.0 (2×CH), 129.8 (2×CH), 128.2 (2×CH), 127.3 (2×CH), 126.3 (CH), 126.2 (CH), 93.6 (CH), 75.7 (CH$_2$), 57.8 (C), 53.9 (CH), 36.7 (CH$_2$), 35.4 (CH$_2$), 33.2 (CH$_2$)

Elemental analysis: Calcd for C$_{20}$H$_{20}$O: C, 86.92; H, 7.29. Found: C, 86.81; H, 7.42(%).

Example 4

Preparation of 8-diphenylmethyl-7-[(2'R)-2'-octyloxy]-bicyclo[3.3.0]-1-oxaoctane (16)

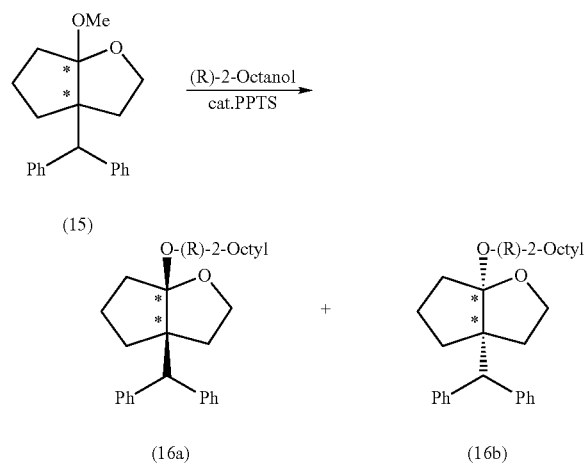

A solution of 66.3 mg (0.24 mmol) of the compound (15) in 1 ml of methylene chloride was added dropwise to a solution of 26.0 mg (0.2 mmol) of (R)-(-)-2-octanol containing 5.0 mg (0.02 mmol) of pyridinium p-toluenesulfonate (PPTS) at 0° C. The mixture was stirred at room temperature for 30 minutes. The reaction solution was washed with saturated brine, dried over anhydrous potassium carbonate, and filtered. The filtrate was concentrated under reduced pressure. The resulting residue was purified by silica gel column chromatography (n-hexane:ethyl acetate 19:1) to obtain 76.6 mg (0.189 mmol, 94%) of a compound (16) as a colorless oil. The compound was separated into diastereomers by silica gel column chromatography (n-hexane:ethyl acetate 1:3) to obtain two types of optically active compounds of 16a and 16b. The yields of 16a and 16b are respectively 29.1 mg (38%) and 32.2 mg (42%).

The properties data of the resulting compounds (16a and 16b) are shown as follows.

(16a: 8-diphenylmethyl-7-[(2'R)-2'-octyloxy]-bicyclo[3.3.0]-1-oxaoctane)

$^1$H-NMR (CDCl$_3$, δppm): 7.41 (brd, J=7.6 Hz, 4H), 7.28-7.08 (m, 6H), 4.57 (s, 1H), 3.94 (tq, J=6.0, 6.0 Hz, 1H), 3.84 (t, J=7.2 Hz, 2H), 2.67 (ddd, J=6.2, 9.2, 13.6 Hz, 1H), 1.96 (t, J=7.2 Hz, 2H), 1.84-1.70 (m, 2H), 1.68-1.25 (m, 11H), 1.20 (d, J=6.0 Hz, 3H), 1.13-0.98 (m, 1H), 0.94 (ddd, J=9.5, 9.5, 12.0 Hz, 1H), 0.89 (t, J=6.5 Hz, 3H)

Elemental analysis: Calcd for C28H$_{38}$O$_2$: C, 82.71; H, 9.42. Found: C, 82.49; H, 9.64(%).

Optical rotation: ([α]$_D^{22}$=152.940° (c=2.21, CHCl$_3$)

(16b: 8-diphenylmethyl-7-[(2'S)-2'-octyloxy]-bicyclo[3.3.0]-1-oxaoctane)

$^1$H-NMR (CDCl$_{13}$, δppm): 7.41 (brd, J=7.6 Hz, 4H), 7.28-7.08 (m, 6H), 4.55 (s, 1H), 3.85 (tq, J=6.0, 6.0 Hz, 1H), 3.88-3.76 (m, 2H), 2.63 (ddd, J=6.2, 8.8, 13.6 Hz, 1H) 1.99 (ddd, J=8.0, 8.0, 12.0 Hz, 1H), 1.93 (ddd, J=5.3, 6.7, 12.0 Hz, 1H), 1.88-1.71 (m, 2H) 1.70-1.29 (m, 11H) 1.19 (d, J=6.0 Hz, 3H), 1.13-0.89 (m, 2H), 0.92 (t, J=6.5 Hz, 3H)

Elemental analysis: Calcd for C$_{28}$H$_{38}$O$_2$: C, 82.71; H, 9.42. Found: C, 82.49; H, 9.71(%).

Optical rotation: [α]$_D^{22}$=+118.59° (c=2.27, CHCl$_3$)

Example 5

Preparation of 7R,8R-8-diphenylmethyl-7-methoxy-bicyclo[3.3.0]-1-oxaoctane (14a)

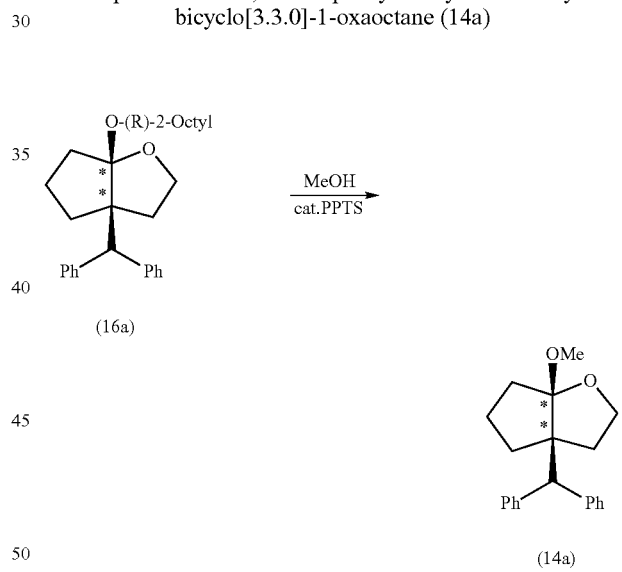

252 my (0.62 mmol) of the compound (16a) obtained above was dissolved in 5 ml of anhydrous ethanol. 16 mg (0.062 mmol) of pyridinium p-toluenesulfonate (PPTS) was added to the solution and the mixture was refluxed for 12 hours. After cooling to room temperature, 20 mg (0.14 mmol) of potassium carbonate was added to the reaction solution and the mixture was stirred for 15 minutes. The reaction solution was poured into water. The mixture was extracted with 60 ml of diethyl ether three times. The organic layer was collected, dried over anhydrous potassium carbonate, and filtered. The filtrate was concentrated under reduced pressure. The resulting residue was purified by silica gel column chromatography (n-hexane:ethyl acetate 10:1) to obtain 162 mg of a target product (14a). The yield was 85%.

Optical rotation: [α]$_D^{23}$=−208.09° (c=0.875, CHCl$_3$)

Example 6

Preparation of 7S,8R-8-diphenylmethyl-7-methoxy-bicyclo[3.3.0]-1-oxaoctane (14b)

7S,8R-8-diphenylmethyl-7-methoxy-bicyclo[3.3.0]-1-oxaoctane (14b) was obtained from the compound (16b) in the same manner as in Example 5.

Optical rotation: $[\alpha]_D^{23}=+208.09°$ (c=0.875, CHCl$_3$)

Example 7

Preparation of 8R-8-diphenylmethyl-bicyclo[3.3.0]-1-oxa-6-octene (15a)

A target product (15a) was obtained from the compound (14a) obtained in Example 5 in the same manner as in Example 3.

Optical rotation: $[\alpha]_D^{23}=-8.34°$ (c=2.805, CHCl$_3$)

Example 8

Preparation of 8S-8-diphenylmethyl-bicyclo[3.3.0]-1-oxa-6-octene (15b)

A target product (15b) was obtained from the compound (14b) obtained in Example 6 in the same manner as in Example 3.

Optical rotation: $[\alpha]_D^{23}=+8.34°$ (c=2.805, CHCl$_3$)

Example 9

Preparation of (7R,8S)-8-diphenylmethyl-7-(3b,5a-cholestanoiloxy)-bicyclo[3.3.0]-1-oxaoctane (17)

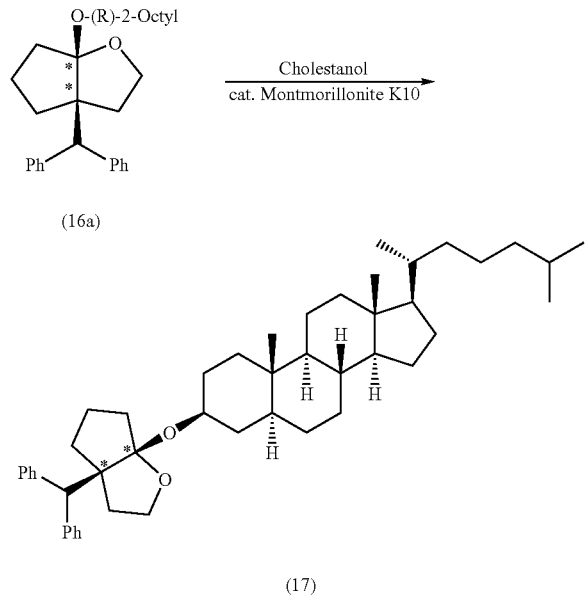

A solution of 30 mg (0.074 mmol) of the compound (16a) and 143.6 mg (0.37 mmol) of cholestanol in 0.5 ml of methylene chloride was added to a solution of 30 mg of montmorillonite K10 in 0.5 ml of methylene chloride at room temperature. The mixture was stirred for two hours at the same temperature. The reaction solution was filtered through celite. The filtrate was concentrated under reduced pressure. The resulting residue was purified by silica gel column chromatography (n-hexane:ethyl acetate=15:1) to obtain 30.7 mg of a target product (17) as colorless plate crystals. The yield was 62%.

The properties data of the compound (17) are shown as follows.

$^1$H-NMR (CDCl$_3$, δppm): 7.40 (brd, J=7.5 Hz, 4H), 7.27-7.08 (m, 6H), 4.57 (s, 1H), 3.83 (t, J=7.3 Hz, 2H), 3.72-3.61 (m, 1H), 2.70-2.61 (m, 1H), 1.99-0.58 (m, 38H), 0.91 (d, J=6.6 Hz, 3H), 0.88 (d, J=6.3 Hz, 6H), 0.85 (s, 3H), 0.66 (s, 3H)

Elemental analysis: Calcd for C$_{47}$H$_{68}$O$_2$: C, 84.88; H, 10.31. Found: C, 84.88; H, 10.35(%).

Optical rotation: $[\alpha]_D^{22}=-137.87°$ (c=1.60, CHCl$_3$)

The crystals of the resulting compound (17) were analyzed by X-ray analysis to determine the absolute configuration of the compound (16a). The absolute configurations and relative configurations of the other compounds were also determined based on this absolute configuration.

Example 10

Preparation of 8-diphenylmethyl-7-(2'R-2'-alkoxy)-bicyclo[3.3.0]-1-oxaoctane (18a) and 8-diphenylmethyl-7-(2'S-2'-alkoxy)-bicyclo[3.3.0]-1-oxaoctane (18b)

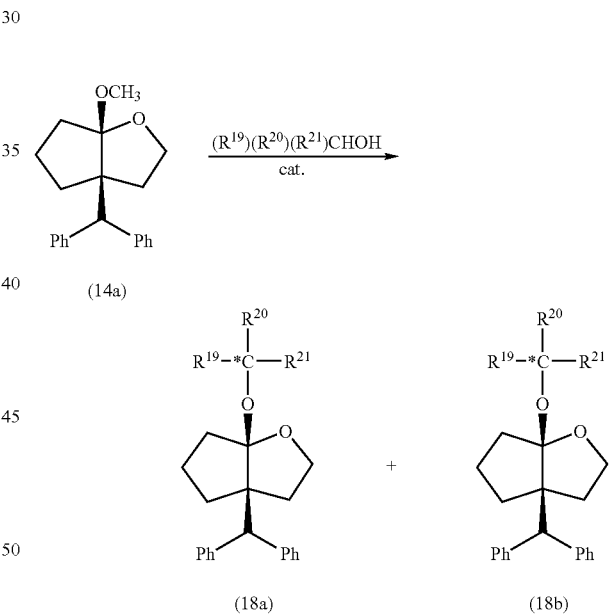

The acetal exchange reactions were carried out by reacting 7-methoxy-8-diphenylmethyl-bicyclo[3.3.0]-1-oxaoctane (14a) obtained above with various alcohols of the formula (R$^{19}$)(R$^{20}$)(R$^{21}$)COH. There are two common processes for the acetal exchange reaction as follows.

(Process 1)

A methylene chloride solution of the compound (14a) was added to the same weight of a methylene chloride solution of an alcohol (5-10 equivalents for the compound (14a)) containing montmorillonite K10 and molecular sieve 4A at room temperature. The mixture was stirred for 7-10 hours at the same temperature. The reaction solution was filtered through celite. The filtrate was concentrated under reduced pressure.

The resulting residue was purified by silica gel column chromatography (n-hexane:ethyl acetate=19:1) to obtain an isomer mixture of a target product. Furthermore, the resulting isomer mixture was separated into individual diastereomers (18a and 18b) by silica gel column chromatography (n-hexane:toluene=1:2.5-3)

(Process 2)

An alcohol (10-20 equivalents for the compound (14a)) and pyridinium p-toluenesulfonate were added in that order to a benzene solution of the compound (14a). The mixture was refluxed for 10-20 hours. A small amount of potassium carbonate was added to the reaction solution and the mixture was stirred at room temperature. The reaction solution was poured into water and the mixture was extracted with diethyl ether. The organic layer was washed with saturated brine, dried over anhydrous potassium carbonate, and filtered. The filtrate was concentrated under reduced pressure. The resulting residue was optionally purified by silica gel column chromatography (n-hexane:ethyl acetate=19:1) and separated into diastereomers (18a and 18b) using silica gel column chromatography (n-hexane:toluene=1:2.5-3).

The resulting compounds were identified using the measurements of FT-IR, $^1$H-NMR, and $^{13}$C-NMR spectra and the elemental analysis.

The types of alcohols used, the Rf values of the optically active compounds (18a and 18b) obtained by silica gel thin-layer chromatography (TLC), the Rf value differences between these compounds (ΔRf values) and the eluates of Example 10 are shown in Table 1.

-continued

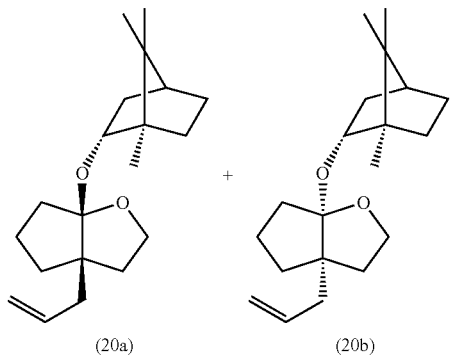

(20a)       (20b)

2.54 g (16.5 mmol) of ((1S)-endo)-(-)-borneol (19) was added to 35 ml of a toluene solution containing 3 g (16.5 mmol) of an acetal (8) and 39 of molecular sieve 5A at room temperature. The mixture was stirred for 10 hours at 110° C. The reaction solution was filtrated. The filtrate was concentrated under reduced pressure to obtain 4.3 g of a residue. The resulting residue was purified by silica gel column chromatography (n-hexane:diethyl ether=40:1) to obtain a target isomer mixture. Furthermore, the resulting isomer mixture was separated into individual diastereomers (20a and 20b) by

TABLE 1

| | $(R^{19})(R^{20})(R^{21})$COH | | | Separation by TLC | | |
|---|---|---|---|---|---|---|
| No. | $R^{19}$ | $R^{20}$ | $R^{21}$ | Compound (18a) | Compound (18b) | ΔRf value | Eluate |
| 1 | n-$C_3H_7$ | $CH_3$ | H | 0.526 | 0.481 | 0.045 | 200/100 (a) |
| 2 | n-$C_4H_9$ | $CH_3$ | H | 0.475 | 0.393 | 0.082 | 175/100 (a) |
| 3 | n-$C_5H_{11}$ | $CH_3$ | H | 0.535 | 0.445 | 0.091 | 150/100 (a) |
| 4 | n-$C_6H_{13}$ | $CH_3$ | H | 0.541 | 0.442 | 0.099 | 133/100 (a) |
| 5 | n-$C_9H_{19}$ | $CH_3$ | H | 0.580 | 0.433 | 0.147 | 125/100 (a) |
| 6 | n-$C_{13}H_{27}$ | $CH_3$ | H | 0.541 | 0.388 | 0.153 | 120/100 (a) |
| 7 | n-$C_3H_7$ | $C_2H_5$ | H | 0.553 | 0.505 | 0.048 | 100/100 (b) |
| 8 | n-$C_4H_9$ | $C_2H_5$ | H | 0.577 | 0.525 | 0.052 | 100/100 (b) |
| 9 | n-$C_5H_{11}$ | $C_2H_5$ | H | 0.594 | 0.530 | 0.064 | 100/100 (b) |
| 10 | n-$C_9H_{19}$ | $C_2H_5$ | H | 0.649 | 0.576 | 0.073 | 100/100 (b) |
| 11 | $CH_3$ | $CF_3$ | H | 0.420 | 0.387 | 0.033 | 100/300 (c) |
| 12 | n-$C_3H_7$ | $CF_3$ | H | 0.466 | 0.413 | 0.053 | 100/300 (c) |
| 13 | n-$C_4H_9$ | $CF_3$ | H | 0.520 | 0.429 | 0.091 | 100/300 (c) |
| 14 | n-$C_5H_{11}$ | $CF_3$ | H | 0.482 | 0.371 | 0.111 | 100/300 (c) |

Example 11

Preparation of 8-(2-propenyl)-7-[((1S)-endo-(-)-bornyloxy]-bicyclo[3.3.0]-1-oxaoctane (20a, 20b)

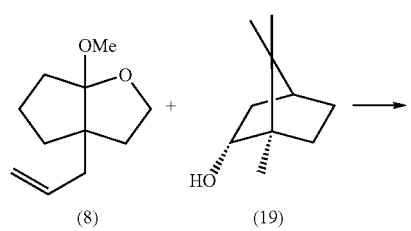

(8)       (19)

silica gel column chromatography (n-hexane:diisopropyl ether=1:40). The yields of 20a and 20b are respectively 1.91 g (38%) and 2.11 g (42%).

The properties data of the resulting compounds (20a and 20b) are shown as follows.

(20a: 8-(2-propenyl)-7-[((1S)-endo)-(-)-bornyloxy]-bicyclo[3.3.0]-1-oxaoctane)

FT-IR (nujor): 3,180, 2,960, 2,880, 1,645, 1,480, 1,460, 1,400, 1,375, 1,330, 1,310, 1,240, 1,195, 1,125, 1,060, 1,025, 960, 948, 920 cm$^{-1}$ $^1$H-NMR (CDCl$_3$, δppm): 5.88 (ddd, J=7.0, 10.0, 16.5 Hz, 11), 5.09-5.04 (m, 2H), 4.10-3.98 (m, 1H), 3.92-3.70 (m, 2H), 2.27 (m, 1H), 2.22-0.95 (m, 16H), 0.84 (s, 6H), 0.80 (s, 3H)

EI-MS: m/z 304 (M$^+$)

Optical rotation: [α]$_D^{25}$=−74.18° (c=1.05, CHCl$_3$)

(20b: 8-(2-propenyl)-7-[((1S)-endo)-(-)-bornyloxy]-bicyclo[3.3.0]-1-oxaoctane)

FT-IR (nujor): 3,180, 2,960, 2,880, 1,645, 1,478, 1,460, 1,395, 1,375, 1,325, 1,310, 1,240, 1,195, 1,120, 1,058, 1,025, 960, 948, 920 cm$^{-1}$ $^1$H-NMR (CDCl$_3$, δppm): 5.88 (ddd, J=7.0, 10.0, 16.5 Hz, 1H), 5.09-5.04 (m, 2H), 3.92-3.70 (m, 3H), 2.27 (m, 1H) 2.22-0.95 (m, 16H), 0.84 (s, 6H), 0.80 (s, 3H)

EI-MS: m/z 304 (M$^+$)

Optical rotation: $[\alpha]_D^{25}$=+5.56° (c=0.84, CHCl$_3$)

INDUSTRIAL APPLICABILITY

The present invention provides a novel optical resolving reagent which can optically resolve an alcohol having an asymmetric carbon atom in the molecule easily and industrially advantageously. The present invention also provides a method for optically resolving an alcohol which can optically resolve a diastereomer mixture of an alcohol that has conventionally been difficult to be optically resolved in the industrial scale easily and industrially advantageously with the optical resolving reagent of the present invention. The method for optical resolution of the present invention, highly common and highly flexible, can be applied to optical resolution of a broad variety of alcohols.

The invention claimed is:

1. A method for optically resolving an alcohol of the formula (3):

(R$^{11}$)(R$^{12}$)(R$^{13}$)COH    (3)

wherein R$^{11}$, R$^{12}$, and R$^{13}$ individually represent a hydrogen atom or a substituted or unsubstituted alkyl group having 1-20 carbon atoms, provided that at least one of R$^{11}$, R$^{12}$, and R$^{13}$ is not a hydrogen atom, the method comprising:

a step of reacting at least one of the compounds having the following formula (1) or (2):

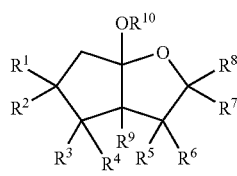

(1)

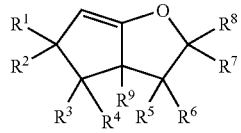

(2)

wherein R$^1$-R$^8$ individually represent a hydrogen atom or an alkyl group having 1-20 carbon atoms, R$^9$ represents a substituted or unsubstituted alkyl group having 1-20 carbon atoms, a substituted or unsubstituted alkenyl group having 1-20 carbon atoms, formyl group, or an acyl group, and R$^{10}$ represents an alkyl group having 1-6 carbon atoms, provided that the R$^9$ group and the OR$^{10}$ group are cis-configured with an optical isomer mixture of an alcohol having an asymmetric carbon atom in the molecule of the formula (3) to obtain a diastereomer mixture of the formula (4):

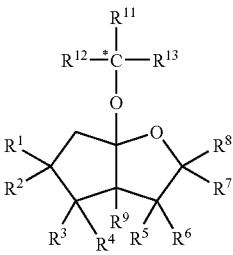

(4)

wherein R$^1$-R$^{13}$ are the same as defined above, * represents an asymmetric carbon atom, and a R$^9$ group and a OC(R$^{11}$)(R$^{12}$)(R$^{13}$) group are cis-configured, a step of separating the resulting diastereomer mixture of the formula (4) into individual diastereomers, and a step of reacting the separated diastereomer with an alcohol of the formula, R$^{14}$OH, wherein R$^{14}$ represents an alkyl group having 1-6 carbon atoms, to obtain an optically active alcohol of the formula (3).

2. The method for optical resolution according to claim 1, wherein R$^1$-R$^8$ are individually a hydrogen atom or a methyl group.

3. The method according to claim 1, wherein all the R$^1$-R$^8$ groups are a hydrogen atom.

4. The method according to claim 1, wherein R$^9$ is an allyl group or a group that can be derived from an allyl group.

5. The method according to claim 1, wherein R$^9$ is an allyl group or diphenylmethyl group.

6. The method according to claim 1, comprising optically resolving an optical isomer mixture of an alcohol having an asymmetric carbon atom in the molecule of the formula (3-1):

(R$^{11a}$)(R$^{12a}$)CHOH    (3-1)

wherein R$^{11a}$ and R$^{12a}$ respectively represent the same groups as defined for R$^{11}$ and R$^{12}$ excluding a hydrogen atom.

7. The method according to claim 1, comprising optically resolving an optical isomer mixture of an alcohol having an asymmetric carbon atom in the molecule of the formula (3-2):

(R$^{11b}$)CH$_2$OH    (3-2)

wherein R$^{11b}$ represents a substituted or unsubstituted alkyl group having 1-20 carbon atoms and having an asymmetric carbon atom.

8. The method according to claim 1, wherein an acid catalyst is allowed to be present in the reaction system in the step of reacting one of the compounds of the above formula (1) or (2) with the alcohol of the formula (3) to obtain the compound of the formula (4).

9. The method according to claim 1, comprising using an alcohol of the formula, R$^{14}$OH, wherein R$^{14}$ is the same as R$^{10}$.

10. The method according to claim 1, comprising collecting the compound of the formula (1) or (2) to reuse the compound as an optical resolving reagent after the step of obtaining the optically active alcohol of the formula (3).

* * * * *